United States Patent [19]

Armand et al.

[11] Patent Number: 5,679,839
[45] Date of Patent: Oct. 21, 1997

[54] PREPARATION OF AROMATIC POLYISOCYANATES IN GASEOUS PHASE

[75] Inventors: Jérôme Armand, Lyons; Henri Chiarelli, Communay; Denis Revelant, Genas; Pascal Vacus, Millery, all of France

[73] Assignee: Rhone-Poulenc Chimie, Courbevoie Cedex, France

[21] Appl. No.: 514,630

[22] Filed: Aug. 14, 1995

[30] Foreign Application Priority Data

Aug. 12, 1994 [FR] France ................. 94 10009

[51] Int. Cl.$^6$ .................................. C07C 263/00
[52] U.S. Cl. ....................................... 560/347
[58] Field of Search ............................. 560/347

[56] References Cited

U.S. PATENT DOCUMENTS 5,391,683  2/1995  Joulak et al. ................. 528/67

FOREIGN PATENT DOCUMENTS 0570799  11/1993  European Pat. Off. .
0593334   4/1994  European Pat. Off. .

OTHER PUBLICATIONS

Database WPI, Week 7438, Derwent Publications Ltd., Lond, GB; AN 74–67320V & SU–A–407 567 (Vukhtin et al) Apr. 1974.

Primary Examiner—Samuel Barts
Attorney, Agent, or Firm—Burns, Doane, Swecker & Mathis, L.L.P.

[57] ABSTRACT

Aromatic polyisocyanates are prepared by reacting at least one compound (A), containing at least two primary amine functions and at least one aromatic nucleus, with a relatively modest quantity of phosgene, in the gaseous phase, the amount of phosgene ranging from the stoichiometric amount to a stoichiometric excess of 100% with respect to the number of moles of amine functions of compound (A), carried out in a mixed reactor which comprises a first, homogenizing zone constituting from 20% to 80% of the total volume thereof, and a second, essentially piston flow downstream zone constituting from 80% to 20% of the total volume thereof.

15 Claims, No Drawings

PREPARATION OF AROMATIC POLYISOCYANATES IN GASEOUS PHASE

BACKGROUND OF THE INVENTION

1. Technical Field of the Invention

The present invention relates to the preparation of aromatic compounds substituted by at least two isocyanate functional groups, and, more especially, to the preparation of toluene diisocyanate and isomers thereof, whether alone or in admixture.

2. Description of the Prior Art

The preparation of aromatic compounds bearing one or more isocyanate substituents via the reaction of amines with phosgene, in the gaseous phase, is well known to this art; however, it is commercially significant only for the conversion of monofunctional amines.

The major drawback of the known processes for the production of aromatic polyisocyanates is that they require very large amounts of phosgene compared to the amines employed in the reaction. The formation of polyisocyanates from the corresponding polyamines requires an excess of phosgene on the order of 200 to 300 mole % with respect to the amine functions. This stoichiometric excess of phosgene is known to increase the phosgenation rate. Further, it prevents the formation of undesirable byproducts resulting from the reaction of the amine with the isocyanate and which, other than reducing the yield of polyisocyanate, also frequently present the disadvantage of being solid and blocking the reactors. These problems do not exist when the amine starting materials are aliphatic or aromatic monoamines, or aliphatic polyamines.

However, while large excesses of phosgene are recommended for reaction efficiency, employing such great amounts is undesirable from standpoint of health and safety because of the toxicity of this reactant and the constraints imposed on the use thereof, whether governmental or otherwise. These constraints are all the more severe when even larger amounts of phosgene are used in the production facility.

In the processes comprising reacting polyamines with phosgene in the gaseous phase, it is also required to increase the efficiency of the mixing between the reactants in order to avoid side reactions and to obtain good yields of the desired polyisocyanates.

The use of reactors containing movable stirring means for the reaction mixture is thus desirable. However, this option presents problems associated with the existence of rotating parts in the mechanical stirrer, in particular sealing at the axis of rotation, problems with clogging and then blocking the movable stirrer due to the adhesion of byproducts from side reactions.

The process described in EP-A-0,570,799 does not mandate a reactor of the above type, but requires injection of the reactants into a static mixing zone such that the residence time is 0.1 to 0.3 seconds and the degree of segregation between the reactants is $10^{-3}$. Once homogenized, the reaction mixture is transferred to the reaction zone proper, without retromixing, in which the flow of the reaction mixture is plug or piston flow characterized by a minimal Bodenstein and/or Reynolds number. These features are described as essential because otherwise the reactor can become blocked. The drawback or disadvantage of this type of process is that it requires the presence of a large excess of phosgene, ranging from 150 to 250 mole % with respect to the amine functions.

SUMMARY OF THE INVENTION

Accordingly, a major object of the present invention is the provision of an improved process for the preparation of aromatic compounds substituted by at least two isocyanate functional groups which avoids or conspicuously ameliorates the above disadvantages and drawbacks to date characterizing the state of this art, especially in respect of the requirement for a great excess of phosgene.

Briefly, the present invention features contacting at least one compound (A) containing at least two primary amine functions and at least one aromatic nucleus with phosgene, both reactants being introduced in the gaseous phase, in the presence of a stoichiometric excess of phosgene of between 0% and 100% with respect to the number of moles of amine functions of compound (A), in a mixed reactor comprising a first, homogenizing zone corresponding to 20% to 80% of the total volume of the reactor, and a second zone in which the flow of the reaction medium approximates piston flow, constituting 80% to 20% of the total volume of the reactor.

DETAILED DESCRIPTION OF BEST MODE AND PREFERRED EMBODIMENTS OF THE INVENTION

More particularly according to the present invention, the subject preparative process produces isocyanates corresponding to the transformation of the above amines without the requirement for carrying out the reaction in the presence of a very large excess of phosgene. It has also now been determined that, unexpectedly, the phosgenation of aromatic polyamines can be effected under these conditions without the necessity for a prohibitive increase in reaction time. Further, the isocyanate yield at the reactor outlet is as high as that attained when employing processes utilizing large excesses of phosgene.

One important advantage of the process of the invention is that it is no longer necessary to recycle the unreacted phosgene, in contrast to the processes employing large excesses of this reactant, which require such condition in order to be economically viable. Avoiding the recycling of the phosgene presents the advantage of eliminating a reaction zone in the process which circulates a large quantity of concentrated phosgene, and which may also be under pressure, with all of the associated safety features that this entails.

As indicated above, the process of the invention comprises contacting at least one compound (A) containing at least two primary amine functions and at least one aromatic group or nucleus with phosgene.

In a preferred embodiment of the invention, the process is carried out utilizing at least one compound (A) containing at least two primary amine functions and at least one aromatic $C_6$–$C_{14}$ group, preferably $C_6$–$C_{10}$, which either may or may not be substituted with one or more linear, cyclic or branched, saturated or unsaturated $C_6$–$C_{10}$ hydrocarbon radicals.

Preferably, the above hydrocarbon radical substituents are selected from among alkyl, aryl, alkylaryl and arylalkyl $C_1$–$C_{10}$ radicals, more preferably $C_1$–$C_6$ radicals.

Preferably, compound (A) has the formula (1):

$$H_2N-R-NH_2 \qquad (1)$$

in which R is the saturated or unsaturated aromatic nucleus described above.

In another preferred embodiment of the invention, at least one compound (A) is employed in which the radical R is optionally substituted by one or more $C_1$–$C_{10}$ alkyl radicals, preferably $C_1$–$C_6$ alkyl radicals.

Particularly exemplary radicals R are the benzene and naphthalene nuclei which either may or may not be substituted by one or more methyl, ethyl, propyl, butyl, pentyl or hexyl radicals and/or isomers thereof.

Preferably, the process is carried out employing at least one compound (A) selected from among toluene diamine, xylylene diamine, or phenylene diamine; these compounds can be used alone or in admixture, either with or without the isomers thereof. More preferably, the compound (A) is toluene diamine.

According to one feature of the invention, the reaction is carried out in the presence of an excess of phosgene of between 0% and 100 mole % with respect to the number of amine functions in compound (A).

A particularly advantageous embodiment entails carrying out the reaction in the presence of a stoichiometric excess ranging from 5% to 60 mole % of phosgene, with respect to the same standard described above.

The reactants contacted with each other in the process of the invention, i.e., the at least one compound (A) and the phosgene, can be used alone or in the presence of a diluent. By the term "diluent" is intended a compound which is inert in respect of the reactants and products of the reaction under conditions of the reaction.

In addition to inert gases, in particular nitrogen, the vapor of a solvent for the compound (A) and/or phosgene can be employed as a diluent. The solvent is advantageously selected from among benzene, xylene, orthodichlorobenzene, monochlorobenzene, or any other solvent which is normally utilized in phosgenation reactions, provided that it is stable under the reaction conditions (temperature, residence time, etc.).

When the compound (A) is dissolved in a diluent, it is advantageously present, in particular, in a concentration by weight of from 3% to 30% in the diluent. This concentration preferably ranges from 10% to 20%.

Thus, if a diluent is used with the amine, admixing thereof preferably is carried out before introduction of the reactants into the reactor. In general, the amine is first dissolved in its solvent in the liquid phase. The resulting mixture is then vaporized at the temperature required for the reaction employing any technique known to this art.

The reactants, optionally in the presence of a diluent, are brought into contact with each other in the vapor phase. The reactants are preheated via any known technique to produce vaporized products during their introduction into the reactor. Further, the reaction is carried out under conditions which ensure that the reactants remain in the vapor state.

Normally, the preheating temperature for the reactants is of the same order as that required for carrying out the phosgenation.

In accordance with another feature of the present invention, the reaction is carried out in a mixed reactor comprising a first, homogenizing zone constituting 20% to 80% of the total volume of the reactor, and a second downstream zone in which the flow of the reaction medium is essentially piston flow, constituting 80% to 20% of the total volume of the reactor.

More particularly, the first zone comprises a reactor whose length is of the same order of size as its cross-section. For convenience, the reactor in this first zone is cylindrical in shape, though, of course, any other geometric form (cubic, spherical) with a cross-section which is about the same size as its length would be suitable.

In a preferred embodiment, the first zone constitutes 40% to 80% of the total volume of the reactor.

The reactants are introduced under conditions in which the first zone in the reactor closely corresponds to a homogenizing reactor.

To this end, introduction of the reactants is preferably carried out such as to promote a turbulent area in this zone to provide good homogenization of the reaction mixture.

The introduction of the reactants can be effected in any one of a number of ways. Preferably, means are employed which encourage retromixing of the reactants (or backmixing). Exemplary of such means are nozzles or multijet injectors.

The nozzles can be concentric, i.e., comprising two concentric tubes inserted one into the other, defining a central portion and an annular portion. Compound (A) and the phosgene, optionally in the presence of a diluent, can be introduced into either the annular portion or via the central portion.

Multijet injectors can comprise either a system including a number of jets converging towards one or more central jets, or a number of jets located in different areas of the reactor with different spraying angles and directions to stir the gas streams.

Introduction of the reactants in the vapor phase can be effected into any region of the stirred reaction zone. Thus, the reactants may be introduced into a region which is close to the wall member up to a region close to the center of the reactor.

The first zone may or may not include static means (obstacles, baffles, etc.) which encourage retromixing of the reactants and homogenization of the admixture.

The second zone of the reactor in the process of the invention is characterized in that the flow of the reaction medium therein is close to or "essentially" piston flow. This zone constitutes 80% to 20% of the total volume of the reactor.

This zone of the reactor completes the phosgenation reaction. It also permits maximum conversion to be attained, while minimizing the total volume of the reactor.

It comprises a reactor of a length which is greater than its cross-section. Tube reactors are exemplary thereof, although other geometric shapes are suitable, provided that the above condition is satisfied.

In a preferred embodiment of the invention, the second zone constitutes 60% to 20% of the total volume of the reactor.

This reaction zone can also be lined with internal obstacles or baffles; preferably, it is not.

The reactor employed to carry out the process of the invention preferably does not contain any movable mechanical stirrers, in either the first or second zone.

The reaction of the invention can be carried out in any type of reactor which is fabricated from a material which is compatible with the operating conditions. In particular, the reaction can thus be carried out in a reactor made of glass or steel which may be alloyed or enamelled.

The residence time of the reactants in the reactor comprising the two zones, in particular, advantageously ranges from 1.5 to 30 seconds. Preferably, the residence time ranges from 3 to 15 seconds. It will be appreciated that the residence time in one or the other of the two zones is proportional to the distribution by volume of the two zones with respect to the whole.

It has thus surprisingly been found that carrying out a significant portion of the reaction in a homogenizing reactor does not cause the problems described above which would normally be expected, despite a slight excess of phosgene.

This is all the more surprising since the known processes feature mixing the reactants in as short a time as possible, in order to avoid reaction, this latter being carried out in a different zone of the reactor, where the residence time is up to 10 times greater than that in the initial zone. The zone in which the reaction proper is carried out is characterized by the absence of retromixing of the reactants which was considered to be the origin of blockages. Contrariwise, the present invention reveals that it is of no importance that the major portion of the phosgenation reaction takes place in a reactor where retromixing is carried out. Further, it has also now been determined that the reaction of the invention carried out in a reactor containing two zones can be effected in a residence time on the same order as processes carried out in piston reactors.

Lastly, reactors comprising a region in which the mixture is homogenized improve heat exchanges and avoid the presence of hot spots therein.

The temperature at which the phosgenation reaction of the invention is carried out advantageously ranges from 250° C. to 500° C. Preferably, the reaction temperature ranges from 300° C. to 400° C. By the term "reaction temperature" is intended the temperature in the reactor.

The process of the invention can be carried out under pressure, under reduced pressure or at atmospheric pressure. For example, the pressure in the reactor advantageously ranges from 0.5 to 1.5 bars absolute. Preferably, it is carried out at a pressure close to atmospheric pressure.

Once the phosgenation reaction has been completed, the reaction products obtained, as well as the unreacted reactants, are separated via any technique known to this art.

The isocyanate produced could, for example, be separated by selective condensation in a suitable solvent.

For convenience, the solvent is preferably selected such that its boiling point is greater than the decomposition point of the carbamyl chloride corresponding to the isocyanate formed. In this manner, a subsequent step of decomposing the carbamyl chloride is avoided.

Also, the solvent must preferably condense at a temperature at which the products, in particular the unreacted phosgene and the hydrochloric acid formed, remain in the gaseous state.

The recovered isocyanate is then purified, in particular by distillation.

Regarding the unreacted phosgene, it should be noted that conventional processes recycle this reactant to the reaction zone. Because of the very large excesses of phosgene used, these processes are only economically viable if this compound is recycled. However, in this zone of the process there exists a large quantity of concentrated phosgene, which may be under pressure, presenting a serious problem in respect of the safety conditions which must be observed.

In a particularly advantageous embodiment of the invention, it is no longer necessary to recycle the phosgene. This eliminates a very important source of problems due to the presence of concentrated phosgene in a particular zone of the process.

In a preferred embodiment, the phosgene separated from the reaction products is destroyed or consumed via any known technique, for example by contact with a base such as caustic soda, or with water.

With respect to the hydrochloric acid, this can be separated from the reaction products for exploitation (separation of the phosgene present, for example by absorption and distillation), or destroyed by reaction with a base.

It should be appreciated, however, that recycling the phosgene to the reaction step is also intended and remains within the scope of the present invention.

In this particular case, the phosgene can be separated from the hydrochloric acid by distillation, absorption in a solvent at low temperature or any other means, then recycled to the phosgenation reaction zone.

In order to further illustrate the present invention and the advantages thereof, the following specific examples are given, it being understood that same are intended only as illustrative and in nowise limitative.

EXAMPLE 1

A cylindrical reactor was employed, having a diameter equal to its height and a volume of 0.18 l, charged by a system of injectors located one quarter of the diameter from the center of the reactor (separate jets for the amine/solvent mixture and for the phosgene), connected to and communicating with a 0.12 l tube reactor (30 cm long).

The injection system was of the type described in the article by Matras and Villermaux, *Chem. Ing. Science*, 28, 129 (1973).

The following reagents were introduced into the reactor:

(a) 600 g/h of a gaseous mixture of toluene diamine, 10% by weight, in orthodichlorobenzene, vaporized at 300° C.;

(b) 155 g/h of pure phosgene preheated to 300° C.

The temperature of the reaction mixture in the reactor was 320° C. and the average residence time of the reactants was on the order of 3.2 to 3.9 seconds.

After analysis, a yield of more than 95% of toluene diisocyanate was obtained at the outlet to the reactor and no significant clogging was observed in the reactor after more than one hour of operation.

EXAMPLE 2

A cylindrical reactor was employed, having a diameter equal to its height and a volume of 0.18 l, charged by a system of injectors located one half diameter from the center of the reactor (separate jets for the amine/solvent mixture and for the phosgene), connected to and communicating with a 0.7 l tube reactor (1.4 m long).

The injection system was as described in Example 1.

The following reagents were introduced into the reactor:

(a) 1,100 g/h of a gaseous mixture of toluene diamine, 10% by weight, in orthodichlorobenzene, vaporized at 330° C.; and (b) 196 g/hg of pure phosgene preheated to 330° C.

The temperature of the reaction mixture in the reactor was 350° C. and the average residence time of the reactants was on the order of 5 to 6.5 seconds.

After analysis, a yield of more than 95% of toluene diisocyanate was obtained at the outlet to the reactor and no significant clogging was observed in the reactor after more than one hour of operation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aromatic polyisocyanate, comprising reacting at least one compound (A), containing at least two primary amine functions and at least one aromatic nucleus, with phosgene, in the gaseous phase, the amount of phosgene ranging from the stoichiometric amount to a stoichiometric excess of 100% with respect to the number of moles of amine functions of compound (A), carried out in a mixed reactor which comprises a first zone constituting from 20% to 80% of the total volume thereof, the first zone comprising a reactor of a length which is of the same order of size as its cross-section, and a second, essentially piston flow downstream zone constituting from 80% to 20% of the total volume thereof, the second zone comprising a reactor of a length which is greater than its cross-section.

2. The process as defined by claim 1, wherein the amount of phosgene ranges from a 5% to a 60% stoichiometric excess with respect to the number of moles of amine functions of compound (A).

3. The process as defined by claim 1, said first, homogenizing zone constituting from 40% to 80% of the total volume of said mixed reactor and said second, essentially piston flow downstream zone constituting from 60% to 20% of the total volume thereof.

4. The process as defined by claim 1, said at least one aromatic nucleus of said at least one compound (A) comprising a substituted or unsubstituted $C_6-C_{14}$ aromatic radical.

5. The process as defined by claim 4, said at least one aromatic radical bearing at least one linear, cyclic or branched, saturated or unsaturated $C_1-C_{10}$ hydrocarbon radical.

6. The process as defined by claim 4, said at least one aromatic nucleus comprising a substituted or unsubstituted $C_6-C_{10}$ aromatic radical.

7. The process as defined by claim 1, said at least one compound (A) having the formula (1):

$$H_2N-R-NH_2 \qquad (1)$$

in which R is a substituted or unsubstituted $C_6-C_{14}$ aromatic radical.

8. The process as defined by claim 7, wherein formula (1), R is substituted by at least one $C_1-C_{10}$ alkyl radical.

9. The process as defined by claim 1, said at least one compound (A) comprising toluene diamine, xylylene diamine, phenylene diamine, or mixture or isomers thereof.

10. The process as defined by claim 1, carried out in the presence of at least one diluent for said at least one compound (A) and/or said phosgene.

11. The process as defined by claim 10, carried out in the presence of at least one diluent for said at least one compound (A), the concentration of said at least one compound (A) in said at least one diluent ranging from 3% to 30% by weight.

12. The process as defined by claim 11, said concentration ranging from 10% to 20% by weight.

13. The process as defined by claim 1, the residence time of the reactants in said mixed reactor ranging from 1.5 to 30 seconds.

14. The process as defined by claim 13, the residence time of the reactants in said mixed reactor ranging from 3 to 15 seconds.

15. A process for the preparation of an aromatic polyisocyanate, comprising reacting at least one compound (A), containing at least two primary amine functions and at least one aromatic nucleus, with phosgene, in the gaseous phase, the amount of phosgene ranging from the stoichiometric amount to a stoichiometric excess of 100% with respect to the number of moles of amine functions of compound (A), carried out in a mixed reactor which comprises a first zone constituting from 20% to 80% of the total volume thereof, and a second, essentially piston flow downstream zone constituting from 80% to 20% of the total volume thereof, wherein the residence time of the reactants is proportional to the distribution by volume of the two zones with respect to the whole, so that a significant portion of the reaction is carried out in the first zone under conditions promoting retromixing.

* * * * *